United States Patent [19]

Bradley et al.

[11] Patent Number: 5,583,041
[45] Date of Patent: *Dec. 10, 1996

[54] DEGRADATION OF POLYHALOGENATED BIPHENYL COMPOUNDS WITH WHITE-ROT FUNGUS GROWN ON SUGAR BEET PULP

[75] Inventors: Clifford A. Bradley; Robert D. Kearns; Pauline P. Wood; William E. Black, all of Butte, Mont.

[73] Assignee: Mycotech Corporation, Butte, Mont.

[ * ] Notice: The portion of the term of this patent subsequent to Jan. 11, 2013, has been disclaimed.

[21] Appl. No.: 188,363

[22] Filed: Jan. 27, 1994

Related U.S. Application Data

[63] Continuation of Ser. No. 705,914, May 28, 1991, abandoned.

[51] Int. Cl.$^6$ ................... C02F 1/00; C02F 3/00; C12N 1/22; C07C 7/00
[52] U.S. Cl. .............. 435/262.5; 435/262; 435/252; 435/254.1; 210/610
[58] Field of Search .................. 435/262.5, 264, 435/911, 821, 262, 252, 254.1; 210/610

[56] References Cited

U.S. PATENT DOCUMENTS

| | | |
|---|---|---|
| 4,554,075 | 11/1985 | Chang et al. . |
| 4,711,787 | 12/1987 | Odakra . |
| 4,803,800 | 2/1989 | Romaine et al. . |
| 4,891,320 | 1/1990 | Aust et al. . |
| 5,486,474 | 1/1996 | Bradley et al. ............... 435/262 |

OTHER PUBLICATIONS

Kirk et al (eds) Lignin Biodegradation: Microbiology, Chemistry, and Potential Applications, vol. II. CRC Press, Boca Raton (1980) p. 215.

Keyser et al., "Ligninolytic Enzyme System of *Phanerochaete chrysosporium*: Synthesized in the Absence of Lignin in Response to Nitrogen Starvation", *Journal of Bacteriology*, Sep. 1978, vol. 135, No. 3, pp. 790–797.

Mileski et al., "Biodegradation of Pentachlorophenol by the White Rot Fungus *Phanerochaete chrysosporium*", *Applied and Environmental Microbiology*, Dec. 1988, vol. 54, No. 12, pp. 2885–2889.

Bumpus, John A., "Biodegradation of Polycyclic Aromatic Hydrocarbons by *Phanerochaete chrysosporium*", *Applied and Environmental Microbiology*, Jan. 1989, vol. 55, No. 1, pp. 154–158.

Haemmerli et al., "Oxidation of Benzo(a)pyrene by Extracellular Ligninases of *Phanerochaete chrysosporium*", *The Journal of Biological Chemistry*, 1986, vol. 261, No. 15, pp. 6900–6903.

Roch et al., "Lignin peroxidase production by strains of *Phanerochaete chrysosporium* grown on glycerol", Appl. Microbiol. Biotechnol., (1989) vol. 31, pp. 587–591.

Kirk et al., "Influence of Culture Parameters on Lignin Metabolism by *Phanerochaete chrysosporium*", Arch. Microbiol., (1978), vol. 117, pp. 277–285.

Ferri, F. *Micol. Ital.* 13(2): 25–30 (1984), as Abstract 9847, *Biological Abstracts* 81(2) (1986).

Tien, Ming *CRC Critical Reviews in Microbiology* 15(2): 141–168 (1987).

Rolz, C. et al. *Appl. Microbiol. and Biotechnol.* 25:535–541 (1987).

Agosin, E. and Odier, E. *Appl. Microbiol and Biotechnol.* 21:397–403 (1985).

Aitken, M. E. et al. *Wat. Res.* 23(4):443–450 (1989).

Tengerdy, R. P. *Trends in Biotechnology* 3(4):96–99 (1985).

Bumpus et al. *Science* vol. 228 (1985) pp. 1434–1436.

Bumpus, John A., *Applied and Environmental Microbiology*, vol. 55, Jan. 1989, pp. 154–158.

*Primary Examiner*—Esther M. Kepplinger
*Assistant Examiner*—Timothy J. Reardon
*Attorney, Agent, or Firm*—Elizabeth A. Hanley; Lahive & Cockfield

[57] ABSTRACT

Polyhalogenated biphenyl compounds can be degraded by white-rot fungus grown on a sugar beet pulp substrate. The method is useful for bioremediation of materials contaminated with polyhalogenated biphenyl compounds.

7 Claims, 2 Drawing Sheets

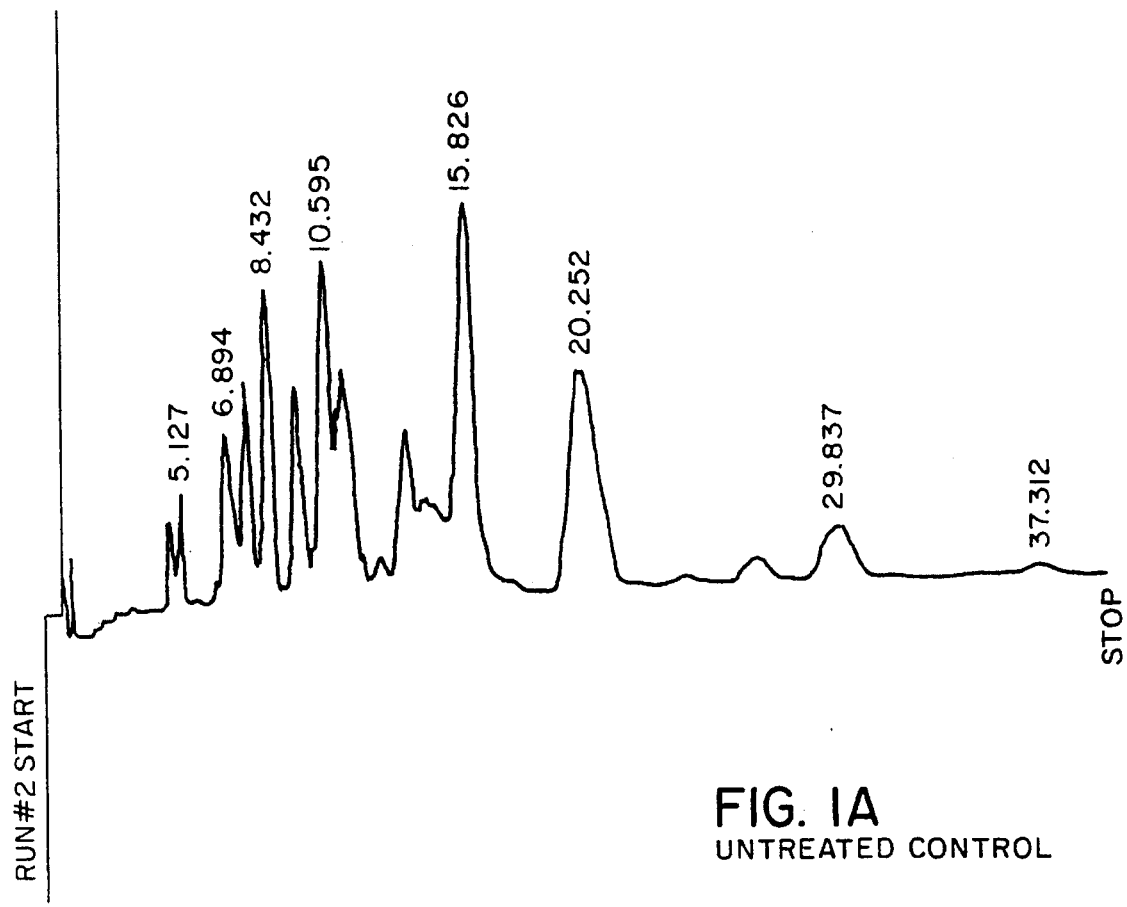
FIG. IA
UNTREATED CONTROL
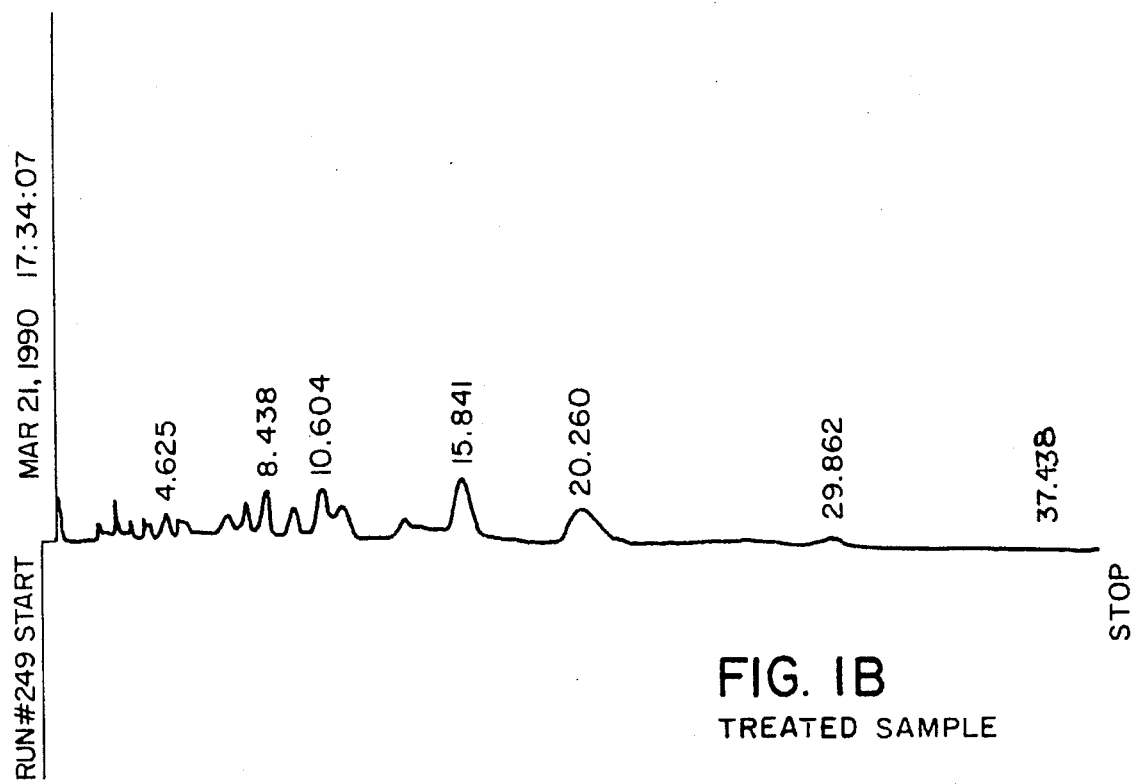
FIG. IB
TREATED SAMPLE

DEGRADATION OF POLYHALOGENATED BIPHENYL COMPOUNDS WITH WHITE-ROT FUNGUS GROWN ON SUGAR BEET PULP

This application is a continuation of application Ser. No. 07/705,914, filed on May 28, 1991, now abandoned.

BACKGROUND OF THE INVENTION

Fungi and bacteria have been used to degrade polychlorinated biphenyl compounds (PCB's). The use of white-rot fungi, for example, to degrade PCB's is described by Aust and Tien, U.S. Pat. No. 4,891,320; Bumpus, J. A. et al. (1985) *Science* 228:1434–1436 and Eaton, D. C. (1985) *Microbial Technology* 7:194–196. These bioremedial processes have significant limitations and generally, they have not been used commercially. Fungal degradation of PCB's has been demonstrated only in small volumes of defined laboratory media with very low concentrations of polychlorinated biphenyl compound (100 to 1000 times less than typical concentration encountered in the field).

Bacterial processes have been limited by the selective degradation of congeners of PCB's. Although significant levels of PCB's can be degraded with bacteria, certain congeners usually are left undegraded. As a result, it would be difficult to achieve EPA mandated clean-up levels which, under the Toxic Substance Control Act (TSCA), currently allow a maximum of 10 ppm total concentration with no congener greater than 2 ppm. In addition, bacterial degradation proceeds rather slowly in field trials. Improved processes for degradation of polyhalogenated biphenyl compounds are needed.

SUMMARY OF THE INVENTION

This invention pertains to a method of degrading polyhalogenated biphenyl compounds in soil, water or other materials. The method comprises contacting the material containing the polyhalogenated biphenyl compounds to be degraded with a culture of white-rot fungus grown on a sugar beet pulp substrate, under conditions which permit the fungus to degrade at least a portion of the polyhalogenated biphenyl compounds in the material. The method can be used in the bioremediation of materials contaminated with polyhalogenated biphenyl compounds such as PCB's and it offers several advantages over other methods of fungal or bacterial degradation of these compounds.

BRIEF DESCRIPTION OF THE FIGURES

FIGS. 1A and 1B are gas chromatograms of polychlorinated biphenyl compounds in control and fungus-treated samples of soil.

DETAILED DESCRIPTION OF THE INVENTION

Figure 2A:
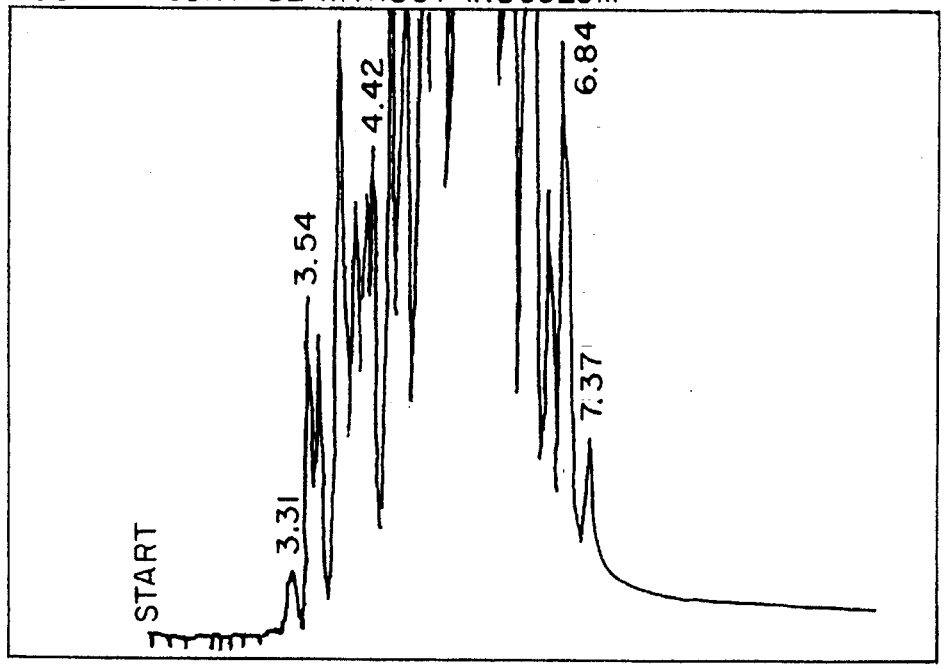
FIGS. 2A and 2B are the same for a different experiment.

In the method of this invention, polyhalogenated biphenyl compounds are degraded by white-rot fungi grown on a solid substrate of sugar beet pulp. The solid state culture of white-rot fungus is contacted with material containing the polyhalogenated biphenyl compounds to be degraded under conditions which permit the fungal enzymes to degrade at least a portion of the polyhalogenated biphenyl compounds.

The white-rot fungus can be selected from the genera Phanerochaete, Phlebia, Trametes and Bjerkandera. Preferred species are *B. adusta* and *P. chrysosporium*. There are an estimated 1700 species of white-rot fungi. However, research on enzymatic lignin degradation has concentrated on one organism; *Phanerochaete chrysosporium*. Lignin-degrading enzymes from this organism have been purified and characterized. A large volume of research literature describes processes for growing *P. chrysosporium* in liquid media for lignin degradation or production of lignin-degrading enzymes. The conventional production of lignin-degrading enzymes in liquid media occurs during secondary metabolism and is initiated by nitrogen or glucose starvation. For instance, in U.S. Pat. No. 4,554,075, Chang et al. describe a process for growing white-rot fungi by carrying growth into secondary metabolism wherein nitrogen starvation occurs. See also Ming Tien in an article in *CRC Critical Reviews in Microbiology*, titled "Properties of Ligninase From *Phanerochaete Chrysosporium* and Their Possible Applications", Volume 15, Issue 2 (1987) at p. 143 and U.S. Pat. No. 4,891,230 to Aust et al.

The growth of white-rot fungus on sugar beet pulp is described in U.S. patent application Ser. No. 07/649,454, filed Feb. 1, 1991, entitled "Method of Cultivating White-Rot Fungi in Solid State Culture", the teachings of which are incorporated by reference herein. The growth of white-rot fungi on sugar beet pulp substrate results in production of lignin-degrading enzymes during the primary metabolic growth phase of the fungi when an abundance of nutrients are available. This is in contrast to conventional culture systems where production takes place during secondary metabolism when nitrogen or carbon may be restricted.

At the conclusion of the growing period, the substrate can be washed with water to bring enzymes into solution. The lignin-degrading enzymes are not irreversibly bound to the substrate using this process. The enzyme-rich solution can be centrifuged and filtered to provide an active, cell-free liquid enzyme preparation containing lignin-degrading enzymes that have been removed from the substrate.

The ability to commercially produce lignin-degrading enzymes during the primary metabolic growth phase and further to produce cell-free lignin-degrading enzymes is an advantage of this invention over conventional solid state or liquid culture process used to produce these enzymes using white-rot fungi.

Sugar beet pulp is used as the substrate material for fungal growth in accordance with this invention. Sugar beet pulp is produced in large amounts and is readily available for high-volume, commercial applications for growing white-rot fungi.

Sugar beet pulp has not been reported as a natural substrate for white-rot fungi. It has a relatively low lignin content of 1% to 3%. White-rot fungi occurs naturally as decay organisms on woody materials with high lignin content such as okra, sugarcane, shredded paper, wood shavings, sawdust, corn cobs and humus. These materials have been used in conventional production of lignin-degrading enzymes.

Sugar beet pulp contains 8–10% protein and up to 5% residual sucrose and is not a carbon and nitrogen limited substrate. Yet, white-rot fungi product lignin-degrading enzymes when grown on sugar beet pulp during the primary metabolic growth phase. Lignin-degrading enzymes are produced by white-rot fungi when grown on sugar beet pulp supplemented with glucose and the additional nitrogen sources peptone (a soluble protein hydrolysate) and yeast extract. This result is unexpected because production of these enzymes using conventional processes typically occurs only with nitrogen or carbon starvation during secondary metabolism. Sugar beet pulp is a byproduct of the processing of sugar beets for sugar (sucrose). In a typical process, sugar beets are sliced and extracted with hot water to recover the sugar. Sugar beet pulp is the residue of sugar beets remaining after the extraction process. In most sugar beet processing plants, the sugar beet pulp is dried and sold as cattle feed. Sugar beet pulp is composed of the following constituents with the typical proportions shown as a percentage on a dry weight basis.

| Mean chemical composition of raw sugar beet pulp | |
| --- | --- |
| Components | Raw Pulp |
| Dry matter | 91.5 |
| Total Nitrogen (× 6.25) | 10.8 |
| Protein Nitrogen (× 6.25) | 9.0 |
| Ashes | 4.3 |
| Organic Matter | 95.7 |
| ADF[a] | 23.3 |
| NDF[b] | 51.9 |
| Lignin | 1.0 |
| Cellulose (ADF-Lignin) | 22.3 |
| Hemicellulose (NDF-ADF) | 28.6 |
| Gross Energy (kcal/kg dry matter) | 4217 |

[a]This is acid detergent fiber.
[b]This is neutral detergent fiber.
*A. Duranl and D. Cherau (1988); "A New Pilot Reactor for Solid State Fermentation: Application to the Protein Enrichment of Sugar Beet Pulp"; Biotechnology and Bioengineering, Vol. 31, pp 476–486.

Particles of sugar beet pulp are typically 0.5 to 1 cm in the largest dimension and irregularly shaped.

Sugar beet pulp can be prepared for use as a solid culture substrate as follows. Dry sugar beet pulp is moistened with one of a number of standard nutrient solutions supportive of fungal growth and then sterilized by autoclaving, e.g., at 125° C., 15 psi for 20 minutes. Other generally accepted methods for sterilization can be used involving different temperatures, pressures and durations as long as the sugar beet pulp is sterilized before inoculation. The sugar beet pulp is then cooled to between 20°–40° C.

An inoculum of white-rot fungi is then aseptically and thoroughly mixed with the cooled sugar beet substrate. The inoculum can be prepared in any conventional manner such as by first selecting a pure culture of a white-rot fungus and maintaining this fungus on nutrient agar slants. Next, the culture on the agar slants is transferred to either a liquid or solid media and grown at 20°–40° C. The media selected varies somewhat depending upon which organism is selected for growth. If a liquid media is selected for growing the inoculum, the liquid inoculum media should contain glucose, a nitrogen source, and nutrient salts. Liquid cultures can be held stationary or agitated during the culture growth phase. If a solid media is selected for growing the inoculum, either sterilized sugar beet pulp, prepared as described above, or other known materials can be used as a substrate. Generally, sufficient inoculum culture is grown to provide approximately 1–20% by volume of the mass of substrate to be inoculated.

According to this invention, the inoculated sugar beet pulp comprises a solid state culture characterized by a solid phase of particles of sugar beet pulp, an aqueous phase sorbed into the particles of the pulp and a gas phase in the interparticle spaces. Moisture content of the sugar beet pulp is 40 to 80%, typically 66% by weight. Optionally, 2–10% sterilized straw can also be added to the sugar beet pulp.

Straw may be added before or, more typically, after the beet pulp is wetted. The straw improves the physical characteristics of the solid culture by increasing the volume and maintaining integrity of interparticle spaces resulting in improved aeration, temperature control and moisture control.

Typically, the fungus grows on the surface of, and penetrates into, the particles of sugar beet pulp.

The inoculated substrate is placed in a vessel designed as a solid culture reactor or in a trench or pile. The shape and dimensions of the vessel used as the solid culture reactor may be varied widely. In one currently developed embodiment, the inoculated substrate is placed in cylindrical or rectangular vessel in a bed approximately 70 cm deep. The vessel is designed so that air at controlled temperature and humidity can be circulated through the bed and appropriate means are provided for this.

In a solid state reactor, the temperature, nutrients, aeration rate and growing period can be varied to regulate the metabolic rate of the culture. Metabolic conditions also can determine the species of enzymes grown. Typically, the temperature of the substrate is maintained between 20°–40° C. depending on the organism and enzyme preparation being produced. A nutrient solution may be added to the substrate as necessary to maintain primary metabolic growth phase. Sufficient conventional nutrient solution is provided during the growing period to prevent nitrogen or carbon starvation or secondary metabolism.

An atmosphere of air, or an artificially created atmosphere having an oxygen concentration of 7–100%, is circulated around and through the substrate during the growing period. An aeration rate of between 0.05 to 20 unit volumes of air per minute per unit volume of substrate may be used. The aeration atmosphere preferably is maintained between 70–99% relative humidity. The relative humidity typically is varied to maintain the absorbed water content of the substrate between about 40–80% initially, and then between about 60–80% at the end of the growing period, with 66–72% being typical. The growing period of the culture is varied from 4 to 30 days, depending on the identity of the organism and the type of enzyme under cultivation.

At the completion of the growing period, the culture comprises a fungal cell mass, unutilized culture substrate, and extracellular enzymes. The whole wet culture can be used without further processing by merely mixing the culture into the material to be degraded.

To produce a cell-free liquid enzyme preparation containing lignin-degrading enzymes, one can extract the culture by mixing it with water. Alternatively, water together with conventional, biologically compatible detergents, such as TWEEN 80, may be used as an extractant. A solution of cell-free enzymes is extracted from the substrate by centrifuging and filtering such as with a filter having, for example, a 0.8 micron pore size.

The method of this invention can be used to degrade polyhalogenated biphenyl compounds in a variety of materials. The method can be used in the bioremediation of soils, aquatic sediments, gravels or other solid materials contaminated with polyhalogenated biphenyl compounds.

For bioremediation of soils, whole wet culture is spread on the soil surface and mixed to thoroughly disperse the particles of white-rot fungus, sugar beet pulp culture through the soil. In laboratory experiments mixing can be accomplished by stirring. In many contaminated sites, polyhalogenated biphenyls have spilled on the surface and contamination is confined to the top 25–50 cm of soil. In these cases the fungus, sugar beet pulp culture is spread on the soil surface and mixed using tilling equipment such as a rototiller, tractor and plow, etc. The methods and implements to accomplish mixing may vary if uniform dispersion of white-rot fungus culture through the soil can be achieved. Where contamination extends too deep for effective mixing or is not accessible to direct mixing as in the case of underwater sediments, the material to be treated may be excavated and mixed with the white-rot fungus, sugar beet pulp culture. The mixture can then be spread in windrows or lifts on a surface or placed in a container such as a lined trench or tank.

The volume of white-rot fungus, sugar beet pulp culture added to a given volume of soil varies with soil characteristics (such as pH and density) concentration of polyhalogenated biphenyls and treatment time. For low concentrations of contaminant generally 100 ppm or less, one application of a volume of fungus culture equal to 25% of the volume of soil may be sufficient to achieve the desired level of remediation. With high concentrations of contaminant or for more rapid degradation, up to 150% volume fungus culture to volume of soil may be necessary. Alternatively, several additions of 25% fungus culture volume at 10 to 20 day intervals may be the most effective.

Moisture content of the mixture of soil and fungus culture is typically maintained at 40–60%, though this may vary depending on water capacity of the soil and volume of fungus culture used. Temperature for treatment must be within a range supportive of growth and metabolism of the species of white-rot fungus being introduced. Generally this is in the range of 10° to 40° C. Time required to achieve a specific level of degradation will vary with contaminant, its concentration, soil characteristic, volume of culture, temperature and moisture. Significant degradation of polyhalogenated biphenyls may be achieved in a few days up to several months.

In addition to the use of whole, wet culture for remediation, cultures may be processed by forming a slurry that can be pumped and mixed more easily in some types of materials. Cultures may also be dried for improved storage and transportation and rehydrated immediately prior to application.

The invention is illustrated further by the following Examples.

EXAMPLE 1

Degradation of PCB's Using Cultures of *Bjerkandera adusta* Grown on Sugar Beet Pulp Polychlorinated biphenyls (PCB's) in soil were degraded by treatment with cultures of *B. adusta* grown on sugar beet pulp. PCB contaminated soil was obtained from an electric utility maintenance yard. The PCB's were a commercial mixture designated as Aroclor 1260. PCB type and concentration in soil was determined by extraction and gas chromatograph according to Environmental Protection Agency (EPA), method 8080. PCB analysis was performed by Mycotech Corporation (Butte, Mont.) and by independent, EPA certified laboratories.

Inoculum cultures of *B. adusta* CBS 595.78 were grown for 4 days at 28° C. in an agitated flask in a nutrient solution of 10 grams/liter glucose, 5 grams/liter peptone and 3 grams/liter yeast extract. Sugar beet pulp was wetted to 70% moisture content with the same high nitrogen medium, sterilized, cooled and inoculated at 10% volume with the inoculum culture. Inoculated sugar beet pulp was incubated for 10 days at 27° C. with an airflow of 0.2 volumes air per volume of culture per minute with the air at approximately 90% relative humidity. At 10 days a sample of the culture was extracted by adding 3 volumes of water per volume of culture and homogenizing with a hand held blender for 20 seconds, centrifuging and filtering through a filter with a 0.8 micron pore size. The cell-free filtrate was assayed for the presence of peroxidase and manganese peroxidase using phenol red and for oxidase using anis alcohol by standard procedures. Extracts contained 18.3 units per ml peroxidase and 99.5 units per ml manganese peroxidase and no other oxidase activity at the time of application to soil.

Whole culture with a moisture content of 78% was mixed at 25% by volume with 50 grams of contaminated soil containing 45 ppm total PCB and the mixture placed in a covered glass bottle and incubated at room temperature for 30 days with periodic addition of water. Controls were prepared by treating contaminated soil with fungus culture that had been destroyed by autoclaving at 121° C. for 20 minutes prior to addition to soil. After 30 days, treated and control soil samples were extracted and assayed for PCB concentration. Controls showed 45 ppm total PCB and treated samples 5 ppm total PCB. Gas chromatograph analysis showed degradation of all PCB congeners in the sample. FIGS. 1A and 1B are chromatographs of the control samples and treated samples showing uniform degradation of the PCB mixture.

EXAMPLE 2

Degradation of PCB's Using Cultures of *B. adusta* Grown on Sugar Beet Pulp

Figure 2B:
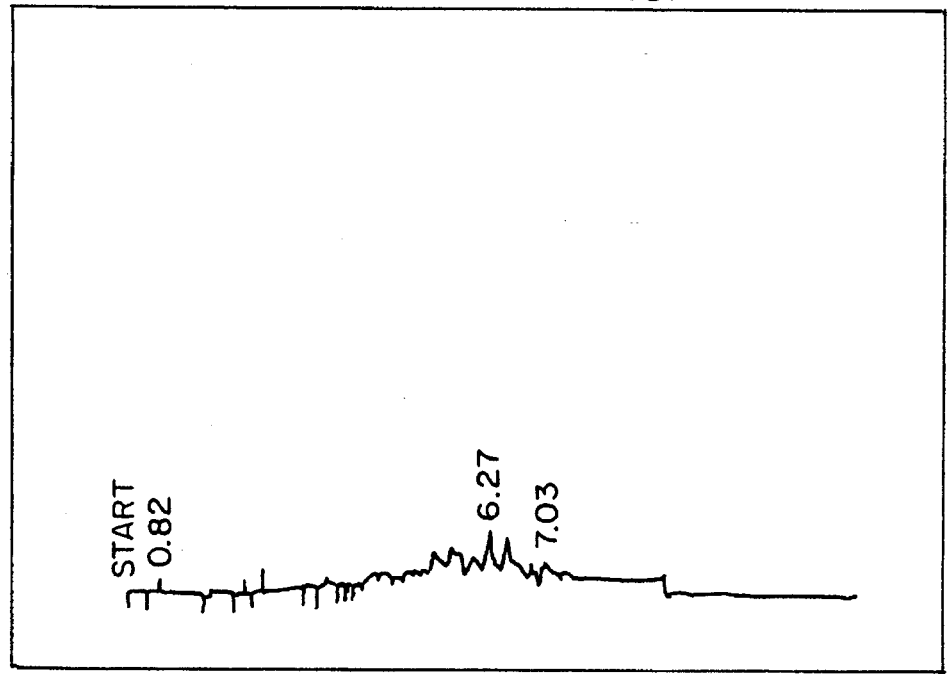

PCB's in contaminated soil were degraded by treatment with cultures of *B. adusta* grown on sugar beet pulp. Cultures were grown and soil treated as described in Example 1 except that soil contamination was 330 ppm total PCB and equal volumes of whole wet culture and soil were used. After 30 days incubation PCB concentration in the treated soil was 15 ppm with uniform reduction of all congeners in the PCB mixture. FIGS. 2A and 2B are chromatographs of extracts of control and treated soil samples.

EXAMPLE 3

Degradation of PCB's in a Time Course Using a Slurry of *B. adusta*, Sugar Beet Pulp Cultures

*B. adusta* sugar beet pulp cultures were prepared as described in Example 1. After 10 days culture time, a slurry of the culture was prepared by adding 3 volumes of water per volume of wet culture. The mixture was homogenized in a blender. The resulting slurry contained 6.7% solids by weight. The slurry can be pumped or poured as a liquid for addition to soil or water. This slurry was stored in the refrigerator and used as the base stock for repeated addition of slurry.

The slurry as prepared contained 7.1 units per ml peroxidase activity and 76.4 units per ml Mn peroxidase activity by phenol red assay.

This experiment was designed as a time course using repeated applications of slurry to eight 50 gram duplicate soil samples. One of the soil samples was extracted without any slurry being added. This sample established the starting concentration. The other 7 soil samples had 50 grams of slurry added to them. After 7 days, all of these samples had approximately 50 grams of slurry added to them. Seven days later, another soil and slurry sample was extracted and analyzed for PCB's. The remaining 5 samples had approximately 50 grams of slurry added. This process was repeated until 35 days had elapsed. No slurry was added to the remaining samples at 35 or 45 days. The results of the time course are summarized in the following table:

| TIME COURSE Slurry Application - B. adusta PCB contaminated soil | | |
| --- | --- | --- |
| Weight Inoculum | Elapsed Time | Concentration ppm |
| 0 g. | 0 days | 325 |
| 50 | 7 | 236 |
| 100 | 14 | 122 |
| 140 | 19 | 66 |
| 275 | 26 | 35 |
| 315 | 35 | 20 |
| 335 | 45 | 12 |
| 335 | 55 | less than 10 |

EXAMPLE 4

The Use of *B. adusta*, Sugar Beet Pulp Culture Slurries to Degrade PCB's in a Field Demonstration

*B. adusta* sugar beet cultures were prepared as described in Example 1. After 10 days culture time, a slurry of the culture was prepared by adding 3 volumes of water to one volume of culture. This preparation was homogenized in a blender for one minute.

The slurry as prepared contained 10.3 units per ml peroxidase activity and 72.7 units per ml Mn peroxidase activity by phenol red assay.

Three soil plots approximately 46 cm in diameter with contamination extending to a depth of 15.5 cm were used for the field demonstration. These plots contained approximately 0.049 cubic meters of soil or 49 liters of soil. Eight liters of slurry were added to two of the plots. Seven days later, slurry was added to the third plot. Samples were taken before slurry addition, at 7 and 14 days. The results are shown in the following table:

| Results of Field Demonstration B. adusta, Sugar Beet Pulp Culture Slurry | | | |
| --- | --- | --- | --- |
| | Initial Conc. ppm | 7 days Elapsed Time | 14 days Elapsed Time |
| Plot 1 | 410 | 370 ppm | 330 ppm |
| Plot 2 | 260 | 230 ppm | 210 ppm |
| Plot 3 | 260 | 230 ppm | |

EXAMPLE 5

The Use of *B. adusta*, Sugar Beet Pulp Cultures to Degrade PCB's in a Field Demonstration

*B. adusta* sugar beet pulp cultures were prepared as described in Example 1. The wet culture contained 18.3 units per ml peroxidase activity and 99.5 units per ml Mn peroxidase activity by phenol red assay.

Three soil plots measuring 2 meters×3 meters with contamination extending 15.5 cm in depth were used for this field demonstration. Approximately 0.55 cubic meters of culture material were mixed into two of the plots. The third plot was treated 7 days later. The plots were sampled for PCB's prior to the addition of the fungus and again after 7 and 14 days elapsed time. The results are shown in the following table:

| Results of Field Demonstration B. adusta, Sugar Beet Pulp Culture | | | |
| --- | --- | --- | --- |
| | Initial Conc. ppm | 7 days Elapsed Time | 14 days Elapsed Time |
| Plot 1 | 150 | 120 ppm | 100 ppm |
| Plot 2 | 210 | 180 ppm | 130 ppm |
| Plot 3 | 190 | 150 ppm | |

EXAMPLE 6

The Use of *B. adusta*, Sugar Beet Pulp Cultures to Degrade PCB's in a Field Demonstration Repeated Additions of *B. adusta*, Sugar Beet Pulp Cultures

*B. adusta* sugar beet cultures were prepared as described in Example 1. The initial wet culture contained 33.2 units per ml peroxidase activity and 85.9 units per ml Mn peroxidase activity by phenol red assay. Subsequent cultures were not assayed for enzyme activity.

Two soil plots approximately 46 cm in diameter with contamination extending to a depth of 15.5 cm were used for the field demonstration. These plots contained approximately 0.049 cubic meters of soil or 49 liters of soil. The whole culture was mixed 100% by volume with the soil. Samples were taken prior to addition of the whole culture and again after 12 days. After the 12 day sample, whole culture was again added to the plots at approximately 50% culture per volume of dirt. The plots were sampled 22 days later. Results of the sampling are shown in the following table. All analyses were performed by an EPA approved laboratory.

| Results of Field Demonstration B. adusta, Sugar Beet Culture Two Applications | | | |
| --- | --- | --- | --- |
| | Initial Conc. ppm | 12 days Elapsed Time | 34 days Elapsed Time |
| Plot 1 | 330 | 280 ppm | 180 ppm |
| Plot 2 | 210 | 180 ppm | 42 ppm |

EXAMPLE 7

The Use of *B. adusta* Sugar Beet Pulp Cultures to Degrade PCB's in a Field Demonstration

*B. adusta* sugar beet pulp cultures were prepared as described in Example 1. Two field soil plots at the site described in Example 1, measuring 46 cm diameter with contamination extending 15.5 cm deep were treated. The first plot contained a beginning PCB concentration of 220 ppm and the second plot 130 ppm. Plots were treated at the rate of 66% volume culture per volume of soil. After 34 days plots showed no evidence of culture substrate or cell mass. At 34 days plots were treated a second time at 70% volume with *B. adusta* sugar beet pulp cultures. Plots were assayed for PCB concentration by an EPA approved laboratory. Assay time intervals beginning from the first addition and PCB concentrations (ppm) are shown in the following table:

Results of Field Demonstration *B. adusta* Sugar Beet Pulp Culture, Two Applications

| | Elapsed Time Days After First Application | | | | | |
|---|---|---|---|---|---|---|
| | 0 | 11 | 23 | 44 | 76 | 98 |
| Plot 1 | 220 | 200 | 180 | 64 | 52 | 35 |
| Plot 2 | 130 | 110 | 100 | 95 | 87 | 12 |

EXAMPLE 8

The Use of *P. chrysosporium*, Sugar Beet Pulp Cultures to Degrade PCB's in a Field Demonstration Single Application of *P. chrysosporium*, Sugar Beet Pulp Cultures Inoculum cultures of *P. chrysosporium* were grown for five days at 28° C. in an agitated flask in a nutrient solution of 10 grams/liter glucose, 5 grams/liter peptone and 3 grams/liter yeast extract. Sugar beet pulp wetted to 70% moisture content with the same high nitrogen medium was autoclaved, cooled and inoculated at 10% volume with the inoculum culture. Inoculated sugar beet pulp was incubated for 7 days at 23° C. with an airflow of 0.2 volumes air per volume of culture per minute with the air at approximately 90% relative humidity. At 7 days, a sample was extracted by adding 3 volumes of water per volume of culture and homogenizing with a hand held blender for 20 seconds, centrifuging and filtering through a filter with a 0.8 micron pore size. The cell free filtrate was assayed for the presence of peroxidase and manganese peroxidase using phenol red. Extracts contained 61 units per ml peroxidase and 64 units per ml manganese peroxidase.

Whole culture with a moisture of 75% was mixed at 25% by volume into a soil plot approximately 46 cm in diameter with contamination extending to a depth of 15.5 cm. The plot contained approximately 49 liters of soil. The soil was contaminated with a mixture of the Aroclors 1254 and 1260 with the majority of the contamination being Aroclor 1260. The soil pH was 8.5. Soil samples were taken at discrete intervals and sent to an EPA approved laboratory for PCB analysis. The results are summarized in the following table:

Results of Field Demonstration *P. chrysosporium*, Sugar Beet Pulp

| Elapsed Time | Concentration in ppm |
|---|---|
| initial | 200 |
| 11 days | 190 |
| 19 days | 180 |
| 50 days | 170 |

EXAMPLE 9

Degradation of PCB's Using Cultures of *P. chrysosporium* Grown on Sugar Beet Pulp PCB's in contaminated soil were degraded by treatment with cultures of *P. chrysosporium* grown on sugar beet pulp. Cultures were grown as described in Example 8 except that the sugar beet pulp was wetted with the salts solution shown in the table below and grown for 6 days at 28° C. Duplicate 50 gram soil samples were prepared. Each sample was mixed with 150% by volume of whole wet fungal culture. The soil contained a mixture of the Aroclors 1242, 1254 and 1260 with 1254 and 1260 being the predominant types. The soil pH was 4.5.

The whole culture was assayed for manganese peroxidase and peroxidase activity as described in Example 8. The culture contained 76 units per ml of manganese peroxidase activity.

At discrete time intervals, a soil sample was sent to an EPA approved laboratory for PCB analysis. The results of those analyses are shown in the following table:

Degradation of PCB's Using *P. chrysosporium* Cultures Grown on Sugar Beet Pulp

| | Elapsed Time | | |
|---|---|---|---|
| Control | 15 days | 35 days | 55 days |
| 310 ppm | 175 ppm | 42 ppm | 18 ppm |

Typical Nutrient Solution Used

| Substance | g/l | Substance | g/l |
|---|---|---|---|
| Glucose | 10.0 | $CaCl_2.2H_2O$ | .03 |
| $NH_4H_2PO_4$ | .05 | Trace Elements | 5 ml stock solution |
| $KH_2PO_4$ | 1.0 | Veratryl Alcohol | 0 or .14 |
| $MgSO_4.7H_2O$ | 1.0 | Peptone | .05 |
| | | Yeast extract | .05 |

EXAMPLE 10

Degradation of PCB's Using Cultures of *P. chrysosporium* Grown on Sugar Beet Pulp PCB's in contaminated soil were degraded with treatments of *P. chrysosporium* grown on sugar beet pulp. Cultures were grown as described in Example 8 except that inoculum cultures were grown in a media containing 0.5 g/l peptone, 0.5 g/l yeast extract and 5 g/l glucose. Duplicate 50 gram soil samples were prepared. The soil was contaminated with the mixture of Aroclors as described in Example 8. Different duplicate soil samples were mixed with 50%, 100% and 150% by volume wet fungal cultures.

The whole culture was assayed for manganese peroxidase and peroxidase activity as described in Example 8. The culture contained 66 per ml of manganese peroxidase activity.

The treated soil was analyzed for PCB's after 14 days. The results of those analyses are shown in the following table:

Degradation of PCB's Using *P. chrysosporium* Grown on Sugar Beet Pulp

| Volume % Fungus | PCB Concentration After 14 days Elapsed Time |
|---|---|
| 0% (control) | 310 ppm |
| 50% | 230 ppm |

| Degradation of PCB's Using *P. chrysosporium* Grown on Sugar Beet Pulp | |
|---|---|
| Volume % Fungus | PCB Concentration After 14 days Elapsed Time |
| 100% | 150 ppm |
| 150% | 101 ppm |

EXAMPLE 11

Degradation of PCB's Using Varying Rates of *P. chrysosporium* Sugar Beet Pulp Culture

*P. chrysosporium* was grown and used to treat 50 gram samples of PCB soil as described in Example 8. Identical soil samples were treated with different volumes of fungus culture and each treatment rate was sampled for PCB concentration at three different time intervals. Treatment rates were 25, 50, 100 and 150% volume of culture per volume of soil. Results are shown in the table below:

| Vol % Fungus Added to Soil | Control | Elapsed Time in Days | | |
|---|---|---|---|---|
| | | 15 | 35 | 55 |
| 0% | 310 | | | |
| 25% | 300 | 305 | 200 | 145 |
| 50% | No Value | 270 | 190 | 130 |
| 100% | 305 | 250 | 130 | 42 |
| 150% | No Value | 175 | 42 | 18 |

NOTE:
PCB concentrations in ppm

EXAMPLE 12

Time Course of PCB Degradation Using *P. chrysosporium* Sugar Beet Pulp Cultures

*P. chrysosporium* was grown as described in Example 8 and used to treat identical 50 gram samples of the PCB contaminated soil also described in Example 8. Soil samples were treated with 150% volume of whole wet *P. chrysosporium* culture and incubated for 10 days. At 10 days an additional 50% volume of culture was added to one half of the 50 gram samples for a total of 200% volume treatment. Samples with 150 and 200% volume of culture were assayed for PCB concentration at 20, 30, 40 and 50 days elapsed time. Results are shown in the table below:

| Elapsed Time in Days | Total Volume of Solid Inoculum | PCB Conc. in ppm |
|---|---|---|
| 0 | 150% | 332 |
| 10 | 150% | 224 |
| 20 | 150% | 154 |
| 20 | 200% | 113 |
| 30 | 150% | 83 |
| 30 | 200% | 73 |
| 40 | 150% | 31 |
| 40 | 200% | 33 |
| 50 | 150% | 13 |
| 50 | 200% | 8 |

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A bioremediation method of degrading a polyhalogenated biphenyl compound in soil or water, comprising:
   a. combining a white-rot fungus and a sugar beet pulp substrate in a high nitrogen fungal culture such that at least one lignin-degrading enzyme is produced during primary metabolism forming a lignin-degrading enzyme-producing white-rot fungal culture; and
   b. mixing the lignin-degrading enzyme-producing white-rot fungal culture with the soil or water containing the polyhalogenated biphenyl compound at a concentration and temperature sufficient to degrade enzymatically at least a portion of the polyhalogenated biphenyl compound in the soil or water.

2. The method of claim 1, wherein the polyhalogenated biphenyl compound is a polychlorinated biphenyl.

3. The method of claim 1, wherein the white rot fungus is from the genus Phanerochaete or Bjerkandera.

4. The method of claim 1, wherein the white rot fungus is *Phanerochaete chrysosporium*.

5. The method of claim 1, wherein the white rot fungus is *Bjerkandera adusta*.

6. A bioremediation method of degrading a polychlorinated biphenyl compound in contaminated soil or water, comprising:
   a. combining a *Bjerkandera adusta* fungus and a substrate of sugar beet pulp in a high nitrogen solid state fungal culture such that at least one lignin-degrading enzyme is produced during primary metabolism forming a lignin-degrading enzyme-producing high nitrogen solid state fungal culture; and
   b. mixing the lignin-degrading enzyme producing *Bjerkandera adusta* fungal culture in admixture with the soil or water containing the polychlorinated biphenyl compound at a concentration and temperature sufficient to degrade enzymatically at least a portion of the polychlorinated biphenyl compound in the soil or water.

7. A bioremediation method of degrading a polychlorinated biphenyl compound in contaminated soil or water, comprising:
   a. combining a *Phanerochaete chrysosporium* fungus and a substrate of sugar beet pulp in a high nitrogen solid state fungal culture such that at least one lignin-degrading enzyme is produced during primary metabolism forming a lignin-degrading enzyme-producing high nitrogen solid state fungal culture; and
   b. mixing the lignin-degrading enzyme producing *Phanerochaete chrysosporium* fungal culture in admixture with the soil or water containing the polychlorinated biphenyl compound at a concentration and temperature sufficient to degrade enzymatically at least a portion of the polychlorinated biphenyl compound in the soil or water.

* * * * *